(12) United States Patent
Landherr et al.

(10) Patent No.: US 10,195,445 B2
(45) Date of Patent: Feb. 5, 2019

(54) BENT LOOP ANTENNA FOR IMPLANTABLE MEDICAL DEVICES

(71) Applicant: Cardiac Pacemakers, Inc., St. Paul, MN (US)

(72) Inventors: Daniel Joseph Landherr, Wyoming, MN (US); Brian D. Allen, Blaine, MN (US); Masoud Ameri, Maple Plain, MN (US); David P. Stieper, North Branch, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/163,997

(22) Filed: May 25, 2016

(65) Prior Publication Data
US 2016/0361550 A1   Dec. 15, 2016

Related U.S. Application Data

(60) Provisional application No. 62/174,187, filed on Jun. 11, 2015.

(51) Int. Cl.
| *A61N 1/372* | (2006.01) |
| *H01Q 1/27* | (2006.01) |
| *H01Q 7/00* | (2006.01) |
| *G06K 9/78* | (2006.01) |
| *G06T 7/12* | (2017.01) |
| *G06T 7/155* | (2017.01) |

(52) U.S. Cl.
CPC .......... *A61N 1/37229* (2013.01); *G06K 9/78* (2013.01); *G06T 7/12* (2017.01); *G06T 7/155* (2017.01); *H01Q 1/273* (2013.01); *H01Q 7/00* (2013.01); *G06T 2207/30024* (2013.01)

(58) Field of Classification Search
CPC ............ A61N 1/37211; A61N 1/37217; A61N 1/37223; A61N 1/37229
See application file for complete search history.

(56) References Cited

U.S. PATENT DOCUMENTS

| 4,570,165 | A * | 2/1986 | Tsurumaru | ................ H01Q 7/00 343/726 |
| 6,958,735 | B2 * | 10/2005 | Handelsman | .......... H01Q 11/14 343/742 |
| 7,109,936 | B2 * | 9/2006 | Mizoguchi | ............. H01Q 1/243 343/702 |
| 7,319,433 | B2 * | 1/2008 | Rosenberg | ............. H01Q 1/243 343/702 |
| 7,342,539 | B2 * | 3/2008 | Rosenberg | ............. H01Q 1/243 343/702 |
| 7,443,300 | B2 * | 10/2008 | Tessier | ...................... G01S 5/14 340/10.1 |

(Continued)

*Primary Examiner* — Eugene T Wu
(74) *Attorney, Agent, or Firm* — Schwegman Lundberg & Woessner, P.A.

(57) ABSTRACT

An implantable medical device can include a device housing including a circuitry module and a header including a header core defining a bore configured to receive a distal end of a lead, an antenna, and a header shell disposed around the header core and the antenna. The antenna can be a closed loop antenna and arranged such that the antenna is positioned within two planes to maximize the area within the closed loop to increase the radiation characteristics of the antenna.

14 Claims, 11 Drawing Sheets

(56) References Cited

U.S. PATENT DOCUMENTS

| | | | |
|---|---|---|---|
| 8,619,000 B2* | 12/2013 | Shinkawa | H01Q 7/00 |
| | | | 343/700 MS |
| 8,854,273 B2* | 10/2014 | Li | H01Q 5/35 |
| | | | 343/741 |
| 8,868,200 B2 | 10/2014 | Abrahamson et al. | |
| 8,912,961 B2* | 12/2014 | Hallivuori | H01Q 1/243 |
| | | | 343/702 |
| 9,325,070 B1* | 4/2016 | Obeidat | H01Q 9/0407 |
| 2005/0007293 A1* | 1/2005 | Handelsman | H01Q 7/005 |
| | | | 343/867 |
| 2005/0140564 A1* | 6/2005 | Deguchi | G06K 7/0008 |
| | | | 343/866 |
| 2008/0021522 A1* | 1/2008 | Verhoef | A61N 1/37229 |
| | | | 607/60 |
| 2011/0196453 A1* | 8/2011 | Abrahamson | A61N 1/37229 |
| | | | 607/60 |
| 2014/0125538 A1* | 5/2014 | Kanj | H01Q 7/06 |
| | | | 343/788 |

* cited by examiner

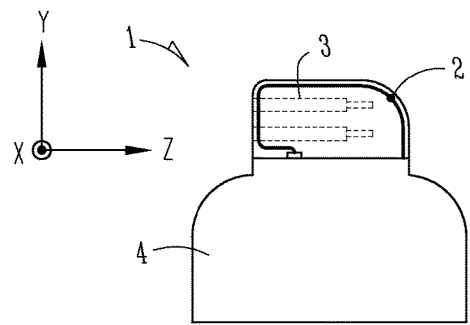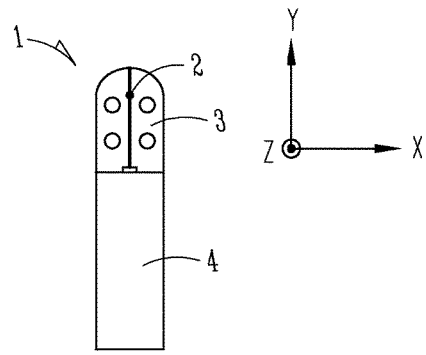
Fig. 1A  Fig. 1B
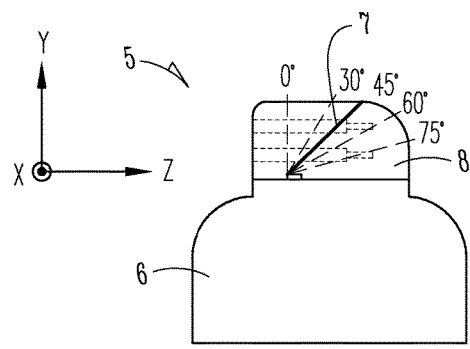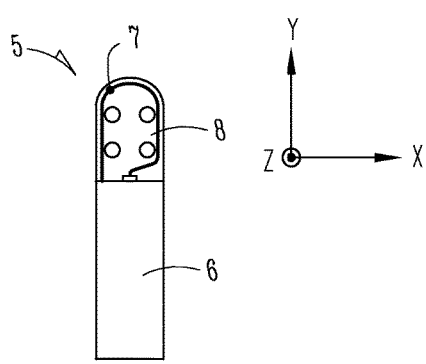
Fig. 2A  Fig. 2B

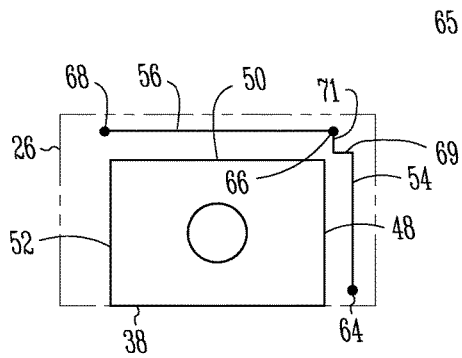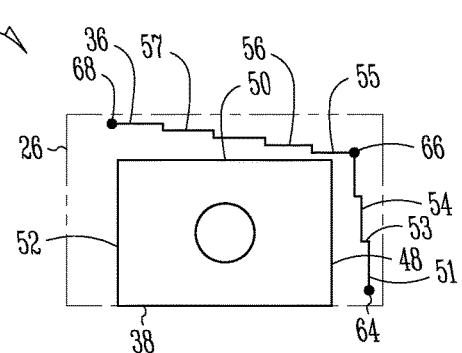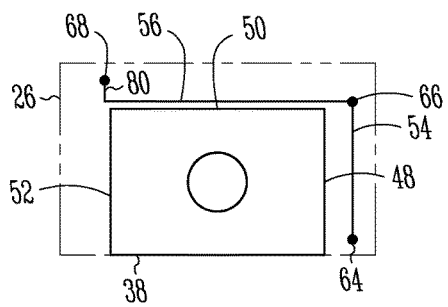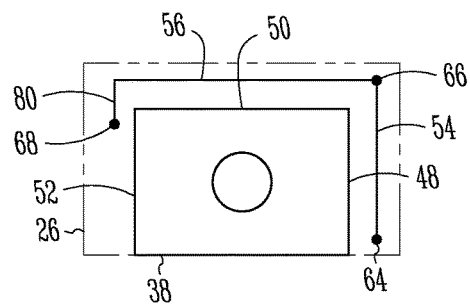

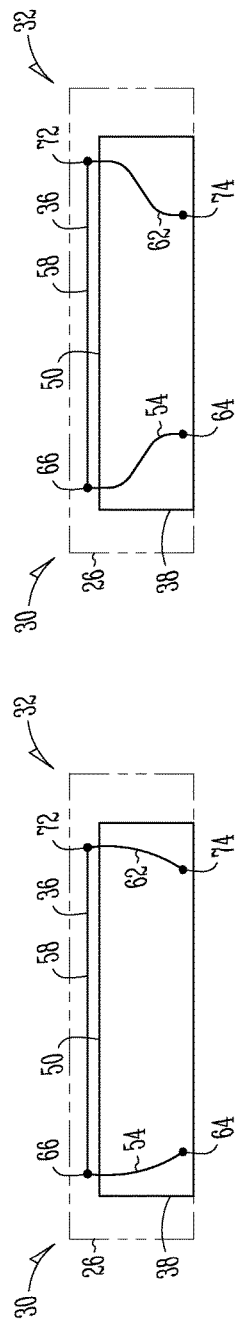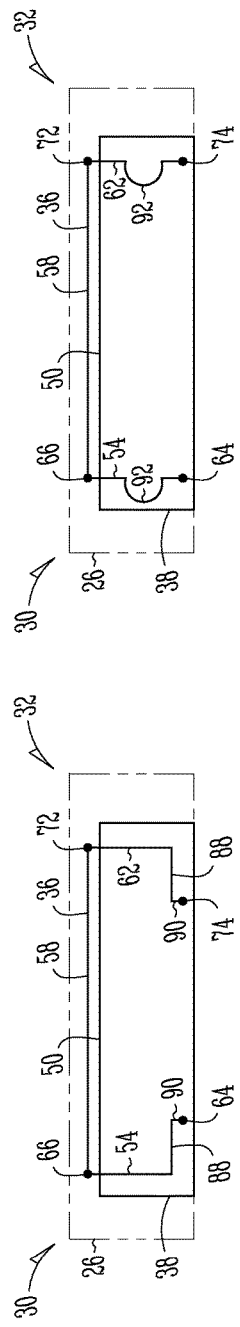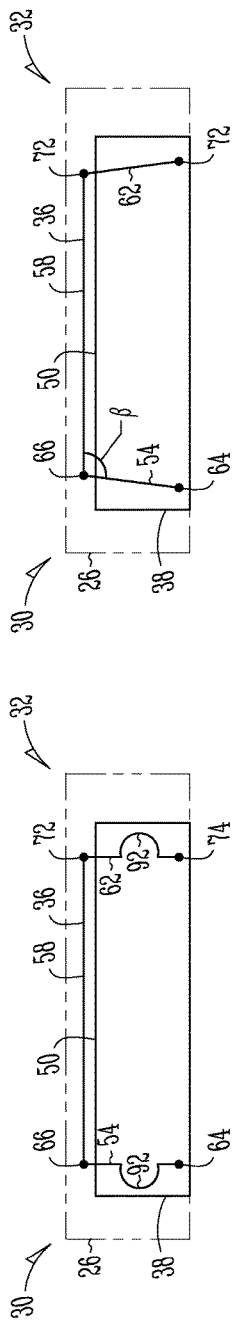

BENT LOOP ANTENNA FOR IMPLANTABLE MEDICAL DEVICES

CLAIM OF PRIORITY

This application claims the benefit of priority under 35 U.S.C. § 119(e) of U.S. Provisional Patent Application Ser. No. 62/174,187, filed on Jun. 11, 2015, which is herein incorporated by reference in its entirety.

TECHNICAL FIELD

The present disclosure relates generally to medical devices and, in particular, to bent loop antennas for implantable medical devices.

BACKGROUND

Implantable medical devices (IMDs) are implantable or partially implantable. Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The devices can be implanted subcutaneously and can include electrodes that are able to sense cardiac signals without being in direct contact with the patient's heart. Other examples of IMDs include implantable diagnostic devices, implantable drug delivery systems, or implantable devices with neural stimulation capability (e.g., vagus nerve stimulator, baroreflex stimulator, carotid sinus stimulator, deep brain stimulator, sacral nerve stimulator, etc.).

Implantable medical devices can be programmed over wireless communication links by means of an external programming device including a transceiver. The implantable medical device can thus, when implanted, be programmed by the physician or caregiver to provide the desired function, for example adjusting the pacing mode of the pacemaker for maintaining a desired heart rate. The importance of having a reliable communication link between the implantable medical device and the external programming device is readily understood. However, the size of the medical implantable device is rather restricted and limits the size of required communication means, such as antennas.

The ability of the antenna to propagate electromagnetic waves can be dependent on the antenna shape and size as well as on the orientation of the antenna. The gain of the closed loop antenna, which is an antenna conventionally used in medical implantable devices, can be dependent on the area enclosed by the antenna wire and the loop antenna radiation pattern thus depends largely on the size and the orientation of the loop formed by the closed loop antenna. As the size of implantable medical devices or portion of the implantable medical device housing the antenna decreases, maintaining or keeping the area enclosed by the antenna as large as possible can become difficult.

SUMMARY

The present disclosure is directed toward a header including a bent loop antenna, IMDs including the bent loop antennas, and methods for making the same. The present inventors have recognized, among other things, as the size of implantable medical devices becomes smaller, maintaining the radiation characteristics of an antenna and maintaining or keeping the area enclosed by the closed loop antenna as large as possible can become more difficult in the confined space. As discussed herein, the radiation characteristics of a closed loop antenna can be related to the area encircled by the antenna. The bent loop antennas of the present disclosure can increase and/or maximize the area encircled by the closed loop antenna in order to obtain the most favorable radiation characteristics for IMDs.

Further, the present inventors have recognized that the quality of an established communication link between the implanted device and an external communicator can be dependent on the orientation of the implanted antenna in relation to an external communicator. For example, a medical device can be assumed to be oriented in a particular direction based on the implant location. The power of the transmitted signal can be optimized when the antenna pattern is oriented with the implant antenna main beam pattern aligned with the external communicator main beam pattern When communicating over a radio frequency link from the implantable medical device to an external communicator, it can be desirable to orient the antenna of the implantable medical device so as to obtain the most favorable radiation characteristics in a direction in which the communication is most often effectuated. In particular, it can be desirable to maximize the radiated electrical field perpendicular from the body part in which the implantable medical device is implanted. In the case of a pacemaker, it can be most desirable to have the electrical field maximum along an axis normal to the chest of the patient.

Previous approaches have included the antenna configurations included in FIGS. 1A, 1B, 2A, and 2B, which are closed loop antennas located in one single plane. In the case of the closed loop antenna illustrated in FIGS. 1A and 1B, the maximum radiation is obtained in the directions perpendicular to the x-axis passing through the center of the loop. That is, the highest radiation is obtained along the y- and z-axes indicated in FIG. 1A. As the medical implantable device 1 is implanted with its principal flat side 4 essentially facing the chest of the patient, the highest E-field strength from the antenna 2 is therefore obtained in a direction along the chest of the patient (z-axis), and not perpendicular thereto.

Another previous approach is illustrated in FIGS. 2A and 2B. The antenna 7 in the implantable medical device 5 in FIGS. 2A and 2B is rotated 90 degrees, as compared to the antenna 2 in FIGS. 1A and 1B. The antenna 7 can be tilted along the y-z plane to make the antenna 7 longer. The maximum radiation is obtained in the directions perpendicular to the z-axis passing through the center of the loop. That is, the highest radiation is obtained along the y- and x-axes indicated in FIG. 2B. However, in both of the closed loop antennas 2, 7 in FIGS. 1A, 1B, 2A, and 2B, the maximum radiation is obtained in only one plane. As discussed herein, because electromagnetic radiation is polarized a signal that is sent will not necessarily be received by the communicator if the communicator antenna and the device antenna are not of the same polarization.

The IMD including the bent loop antenna of the present disclosure provides an antenna that is oriented in two planes, which can receive and generate a quality communication link regardless of the polarization of the electromagnetic radiation sent by the external communicator. Further, the bent loop antenna of the present disclosure maximizes the area formed by the closed loop antenna to maintain and/or increase radiation characteristics, as the available space for the antenna decreases.

To better illustrate the encapsulated filtered feedthrough assemblies, IMDs including the encapsulated filtered feedthrough assemblies, and methods disclosed herein, a non-limiting list of examples is provided here:

Example 1 can include subject matter (such as a device) comprising a device container including an electronic module within the device container, a header, the header including: a header core having a first header surface side, a second header surface side opposite the first header surface side, and a superior header surface side extending between the first and second header surface sides; a closed loop antenna disposed in two different planes, the closed loop antenna, including: a first portion positioned toward a first end of the header, the first portion including a first section extending adjacent to the first header surface side and a second section extending adjacent to the superior header surface side; a second portion positioned toward a second end of the header, the second portion including a third section extending adjacent to the first header surface side, and a fourth section extending adjacent to the superior header surface side; and a third portion connecting the first portion and the second portion; and a header shell disposed around the header core and attached to the device container.

In Example 2, the subject matter of Example 1 can optionally include where the first section extends adjacent to the first header surface from a first connection end to a first transition point and the second section extends adjacent to the superior header surface side from the first transition point to a first intermediate point, and wherein the third section extends adjacent to the first header surface side from a second connection end to a second transition point and the fourth section extends adjacent to the superior header surface from the second transition point to a second intermediate point.

In Example 3, the subject matter of one or both of Examples 1 and 2 can optionally include where the first connection end and the second connection end are electrically coupled to the electronic module.

In Example 4, the subject matter of one or any combination of Examples 1-3 can optionally include where when viewed along a x-y axis, the first portion and the second portion include a bend transitioning the antenna from the first header surface side to the superior header surface side.

In Example 5, the subject matter of one or any combination of Examples 1-4 can optionally include where an angle of the bend, when viewed along the x-y axis, is within a range of about 45 degrees to about 135 degrees.

In Example 6, the subject matter of one or any combination of Examples 1-5 can optionally include where the first section and the third section are along a same side of the header core.

Example 7 can include subject matter (such as a device), or can optionally be combined with the subject matter of one or many combination of Examples 1-6 to include a device container including an electronic module within the device container; a header core having a first header surface side, a second header surface side, and a superior header surface side extending between the first and second header surface sides; a closed loop antenna, including: a first closed loop having a predefined shape and being disposed along the first header surface side and the superior header surface side; and a second closed loop having the predefined shape and positioned adjacent to the header core such that the second closed loop is parallel to the first closed loop and disposed along the first header surface side and the superior header surface side; and a header shell disposed around the header core and attached to the device container.

In Example 8, the subject matter of Example 7 can optionally include where the first closed loop, includes: a first portion positioned toward the first end of the header, the first portion including a first section extending adjacent to the first header surface, and a second section extending adjacent to the superior header surface; a second portion positioned toward the second end of the header, the second portion including a third section extending adjacent to the first header surface, and a fourth section extending adjacent to the superior header surface; and a third portion connecting the first portion and the second portion.

Example 9 the subject matter of one or any combination of Examples 7-8 can optionally include where the second closed loop, includes: a fourth portion positioned toward the first end of the header, the fourth portion including a fifth section extending adjacent to the first header surface, and a sixth section extending adjacent to the superior header surface; a fifth portion positioned toward the second end of the header, the fifth portion including a seventh section extending adjacent to the first header surface, and an eighth section extending adjacent to the superior header surface; and a sixth portion connecting the fourth portion and the fifth portion.

Example 10 the subject matter of one or any combination of Examples 7-9 can optionally include where the first section includes a first connection end and the seventh section includes a second connection end, the first connection end and the second connection end electrically coupled to the electronic module and are located on a same side of the header core.

Example 11 the subject matter of one or any combination of Examples 7-10 can optionally include where the closed loop antenna includes a loop transition section extending between the third section of the first loop and the fifth section of the second loop.

Example 12 the subject matter of one or any combination of Examples 7-11 can optionally include where, when viewed along a x-y axis, the first portion, the second portion, the fourth portion, and the fifth portion include a bend transitioning the antenna from the first header surface side to the superior header surface side.

Example 13 the subject matter of one or any combination of Examples 7-11 can optionally include where the first, third, fifth, and seventh sections are located adjacent to the first header surface side and the second, fourth, sixth, and eight sections are located adjacent to a surface of the header core that is located above the bore and toward the superior header surface side.

Example 14 can include subject matter (such as a method), or can optionally be combined with the subject matter of one or many combination of Examples 1-6 to include providing or obtaining a header core having a first header surface side, a second header surface side, and a superior header surface side extending between the first and second header core sides; coupling at least one closed loop antenna to the header core, the closed loop antenna disposed in two different planes and including: a first portion positioned toward the first end of the header, the first portion including a first section extending adjacent to the first header surface side and a second section extending adjacent to the superior header surface side; a second portion positioned toward the second end of the header, the second portion including a third section extending adjacent to the first header surface side, and a fourth section extending adjacent to the superior header surface side; and a third portion connecting the first portion and the second portion; and disposing a header shell disposed around the header core In Example 15, the subject matter of Example 14 can optionally include the first section extends adjacent to the first header surface from a first connection end to a first transition point and the second section extends adjacent to the superior header surface side from the first transition point to a first intermediate point, and wherein the third section extends adjacent to the first header surface side from a second connection end to a second transition point and the fourth section extends adjacent to the superior header surface from the second transition point to a second intermediate point Example 16 can include subject matter (such as a device), or can optionally be combined with the subject matter of one or many combination of Examples 1-15 to include a device container including an electronic module within the device container, a header, the header including: a header core having a first header surface side, a second header surface side opposite the first header surface side, and a superior header surface side extending between the first and second header surface sides; a closed loop antenna disposed in two different planes, the closed loop antenna, including: a first portion positioned toward a first end of the header, the first portion including a first section extending adjacent to the first header surface side and a second section extending adjacent to the superior header surface side; a second portion positioned toward a second end of the header, the second portion including a third section extending adjacent to the first header surface side, and a fourth section extending adjacent to the superior header surface side; and a third portion connecting the first portion and the second portion; and a header shell disposed around the header core and attached to the device container.

In Example 17, the subject matter of Example 16 can optionally include where
the first section extends adjacent to the first header surface from a first connection end to a first transition point and the second section extends adjacent to the superior header surface side from the first transition point to a first intermediate point, and wherein the third section extends adjacent to the first header surface side from a second connection end to a second transition point and the fourth section extends adjacent to the superior header surface from the second transition point to a second intermediate point.

In Example 18, the subject matter of one or both of Examples 16 and 17 can optionally include where the first connection end and the second connection end are electrically coupled to the electronic module.

In Example 19, the subject matter of one or any combination of Examples 16-18 optionally includes where the first connection end and the second connection end are located on a same side of the header core.

In Example 20, the subject matter of one or any combination of Examples 16-19 can optionally include where when viewed along a x-y axis, the first portion and the second portion include a bend transitioning the antenna from the first header surface side to the superior header surface side.

In Example 21, the subject matter of one or any combination of Examples 16-20 can optionally include where an angle of the bend, when viewed along the x-y axis, is within a range of about 45 degrees to about 135 degrees.

In Example 22, the subject matter of one or any combination of Examples 16-21 can optionally include where the first section and the third section are along a same side of the header core.

In Example 23, the subject matter of one or any combination of Examples 16-22 can optionally include where the first header surface side includes only the first section and the second section of the antenna.

In Example 24, the subject matter of one or any combination of Examples 16-23 can optionally include where the header shell is formed of a dielectric material.

Example 25 can include subject matter (such as a device), or can optionally be combined with the subject matter of one or many combination of Examples 1-24 to include a device container including an electronic module within the device container; a header core having a first header surface side, a second header surface side, and a superior header surface side extending between the first and second header surface sides; a closed loop antenna, including: a first closed loop having a predefined shape and being disposed along a first header surface side and a second header surface side; and a second closed loop having the predefined shape and positioned adjacent to the header core such that the second closed loop is parallel to the first closed loop and disposed along the first header surface side and the second header surface side; and a header shell disposed around the header core and attached to the device container.

In Example 26, the subject matter of Example 25 can optionally include where the first closed loop, includes: a first portion positioned toward the first end of the header, the first portion including a first section extending adjacent to the first header surface, and a second section extending adjacent to the superior header surface; a second portion positioned toward the second end of the header, the second portion including a third section extending adjacent to the first header surface, and a fourth section extending adjacent to the superior header surface; and a third portion connecting the first portion and the second portion.

Example 27 the subject matter of one or any combination of Examples 25 or 26 can optionally include where the second closed loop, includes: a fourth portion positioned toward the first end of the header, the fourth portion including a fifth section extending adjacent to the first header surface, and a sixth section extending adjacent to the superior header surface; a fifth portion positioned toward the second end of the header, the fifth portion including a seventh section extending adjacent to the first header surface, and an eighth section extending adjacent to the superior header surface; and a sixth portion connecting the fourth portion and the fifth portion.

Example 28 the subject matter of one or any combination of Examples 25-27 can optionally include where the first section includes a first connection end and the seventh section includes a second connection end, the first connection end and the second connection end electrically coupled to the electronic module and are located on a same side of the header core.

Example 29 the subject matter of one or any combination of Examples 25-28 can optionally include where the closed loop antenna includes a loop transition section extending between the third section of the first loop and the fifth section of the second loop.

Example 30 the subject matter of one or any combination of Examples 25-29 can optionally include where, when viewed along a x-y axis, the first portion, the second portion, the fourth portion, and the fifth portion include a bend transitioning the antenna from the first header surface side to the superior header surface side.

Example 31 the subject matter of one or any combination of Examples 25-30 can optionally include where the first, third, fifth, and seventh sections are located adjacent to the first header surface side and the second, fourth, sixth, and eight sections are located adjacent to a surface of the header core that is located above the bore and toward the superior header surface side.

Example 32 can include subject matter (such as a method), or can optionally be combined with the subject matter of one or many combination of Examples 1-32, to include providing or obtaining a header core having a first header surface side, a second header surface side, and a superior header surface side extending between the first and second header core sides; coupling at least one closed loop antenna to the header core, the closed loop antenna disposed in two different planes and including: a first portion positioned toward the first end of the header, the first portion including a first section extending adjacent to the first header surface side and a second section extending adjacent to the superior header surface side; a second portion positioned toward the second end of the header, the second portion including a third section extending adjacent to the first header surface side, and a fourth section extending adjacent to the superior header surface side; and a third portion connecting the first portion and the second portion; and disposing a header shell disposed around the header core In Example 33, the subject matter of Example 32 can optionally include the first section extends adjacent to the first header surface from a first connection end to a first transition point and the second section extends adjacent to the superior header surface side from the first transition point to a first intermediate point, and wherein the third section extends adjacent to the first header surface side from a second connection end to a second transition point and the fourth section extends adjacent to the superior header surface from the second transition point to a second intermediate point In Example 34, the subject matter of one or any combination of Examples 32 or 33 can optionally include where the at least one closed loop antenna is a first closed loop antenna, the method includes coupling a second closed loop antenna to the header core.

In Example 35, the subject matter of one or any combination of Examples 32-34 can optionally include where the first closed loop antenna and the second closed loop antenna have a same predefined shape and are coupled to the header core such that the first closed loop antenna is parallel to the second closed loop antenna.

Example 36 can include, or can optionally be combined with any portion or combination or any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

These and other examples and features will be set forth in part in the following Detail Description. This Summary is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

FIG. 1A illustrates a front view of a known antenna configuration of an implantable medical device.

FIG. 1B illustrates a side view of a known antenna configuration of an implantable medical device.

FIG. 2A illustrates a front view of a known antenna configuration of an implantable medical device.

FIG. 2B illustrates a side view of a known antenna configuration of an implantable medical device.

FIG. 12 illustrates a side view of an example of a header including the bent loop antenna.

FIG. 13 illustrates a side view of an example of a header including the bent loop antenna.

FIG. 14 illustrates a side view of an example of a header including the bent loop antenna.

FIG. 15 illustrates a side view of an example of a header including the bent loop antenna.

FIG. 19 illustrates a front view of an example of a header including the bent loop antenna.

FIG. 20 illustrates a front view of an example of a header including the bent loop antenna.

FIG. 21 illustrates a front view of an example of a header including the bent loop antenna.

FIG. 22 illustrates a front view of an example of a header including the bent loop antenna.

FIG. 23 illustrates a front view of an example of a header including the bent loop antenna.

FIG. 24 illustrates a front view of an example of a header including the bent loop antenna.

Figure 3:
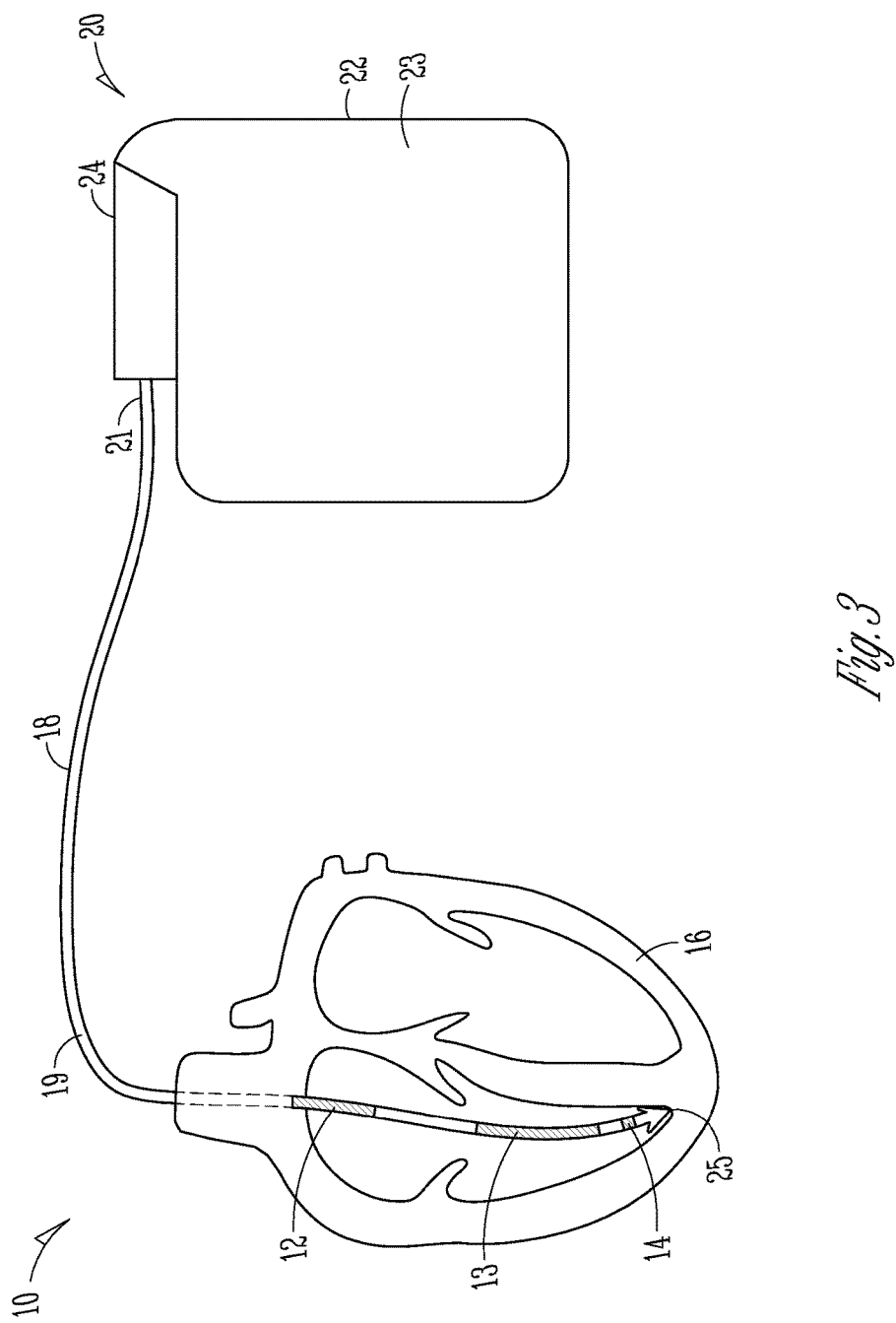
FIG. 3 illustrates an example of an implantable medical device (IMD) and a heart.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

In the following detailed description, reference is made to the accompanying drawings which form a part hereof, and specific embodiments in which the disclosure may be practiced are shown by way of illustration. It is to be understood that other embodiments may be used and structural changes may be made without departing from the scope of the present disclosure.

FIG. 3 illustrates an example of an IMD 10. The IMD 10 can include an electronics unit, such as a pulse generator 20 and at least one lead 18 or electrode. The pulse generator 20 can be, for example, implanted into a subcutaneous pocket made in the upper pectoral region of a patient. Alternatively, the pulse generator 20 can be placed in a subcutaneous or submuscular pocket made in the abdomen, or in other locations of the patient.

The pulse generator 20 generally includes a hermetically sealed device housing, container or can 22 and a header 24. The header 24 can be mechanically and electrically coupled to the device housing 22. The pulse generator 20 can include a power supply such as a battery, a capacitor, and other components housed in the device housing 22. The pulse generator 20 can also include electrical circuitry including an electronic module 23, such as a microprocessor, to provide processing, evaluation, or to determine and deliver electrical shocks or pulses of different energy levels or timing for defibrillation, cardioversion, or pacing to a heart such as in response to cardiac arrhythmia including fibrillation, tachycardia, heart failure, and bradycardia.

In some examples, the pulse generator 20 can include an antenna within the header 24 configured to wirelessly transfer information electromagnetically to an external module. The external module can include a physician programmer, a bedside monitor, or other relatively nearby assembly used to transfer programming instructions or configuration information to the implantable pulse generator 20, or to receive diagnostic information, a disease status, information about one or more physiologic parameters, or the like, from the pulse generator 20. The external module can be communicatively connected to one or more other external assemblies, such as a remote external assembly, located elsewhere (e.g., a server, a client terminal such as a web-connected personal computer, a cellular base-station, or another wirelessly-coupled or wired remote assembly).

The at least one lead 18 can include a lead body 19 having a proximal end 21, where the lead 18 can be coupled to the header 24 of the pulse generator 20. The lead 18 can extend to a distal end 25, which can be coupled with a portion of a heart 16, when implanted. The distal end 25 of the lead 18 can include one or more electrodes 12, 13, 14. The one or more electrodes 12, 13, 14 can be located medially or at other locations along the lead 18. At least one electrical conductor can be disposed within the lead 18, such as to extend from the proximal end 21 to at least one respective electrode(s) 12, 13, 14. The electrical conductors carry electrical current and pulses between the pulse generator 20 and the electrode(s) 12, 13, 14.

In the example illustrated in FIG. 3, the lead 18 can include defibrillation electrodes, such as for delivering defibrillation therapy via a first defibrillation electrode, for example, electrode 12 and/or a second defibrillation, for example, electrode 13. The lead 18 can include additional electrodes, such as for delivering pacing therapy via a pacing/sensing electrode 14. In various examples, the lead 18 can also include an additional tip electrode at the distal end thereof, which in conjunction with the pacing/sensing electrode, for example, electrode 14 can provide for bi-polar pacing and sensing capabilities. While the example in FIG. 3 includes one lead and three electrodes configured to be positioned within the heart, the number and location of the leads and electrodes can vary depending on the type of therapy to be provided and the type of IMD. Further, in some diagnostic devices, the IMD may not include any leads.

In the example shown in FIG. 3, the lead 18 is shown extending into the right ventricle of the heart 16. In other examples, additional leads can be coupled to the pulse generator 20 for implantation within, for example, the right atrium and/or the coronary venous system (e.g., for pacing/sensing of the left ventricle in a bi-ventricular pacing scheme). In still further examples, the lead can be part of a subcutaneous implantable cardioverter defibrillator (S-ICD) that is implantable subcutaneously. The lead is also implanted subcutaneously and the proximal end of the lead is connected to the header. The lead of the S-ICD can include electrodes that do not directly contact the heart. In an example, the lead can include two electrodes to sense ventricular depolarization (e.g., using far-field sensing) and a defibrillation electrode that can be a coil electrode. The S-ICD can provide one or more of cardioversion therapy and defibrillation high energy shock therapy to the heart using the defibrillation electrode and an electrode formed on the device container of the S-ICD. In some examples, the S-ICD can also provide pacing pulses for anti-tachycardia therapy or bradycardia therapy.

In some examples, the IMD 10 can be suitable for use as or with one or more implantable electrical stimulators, such as, but not limited to, pulse generators, neuro-stimulators, skeletal stimulators, central nervous system stimulators, or stimulators for the treatment of pain. The system can also be utilized as a sensor or a receiver. The electrodes can be used, for sensing, pacing, and/or shocking, for example.

Figure 4:
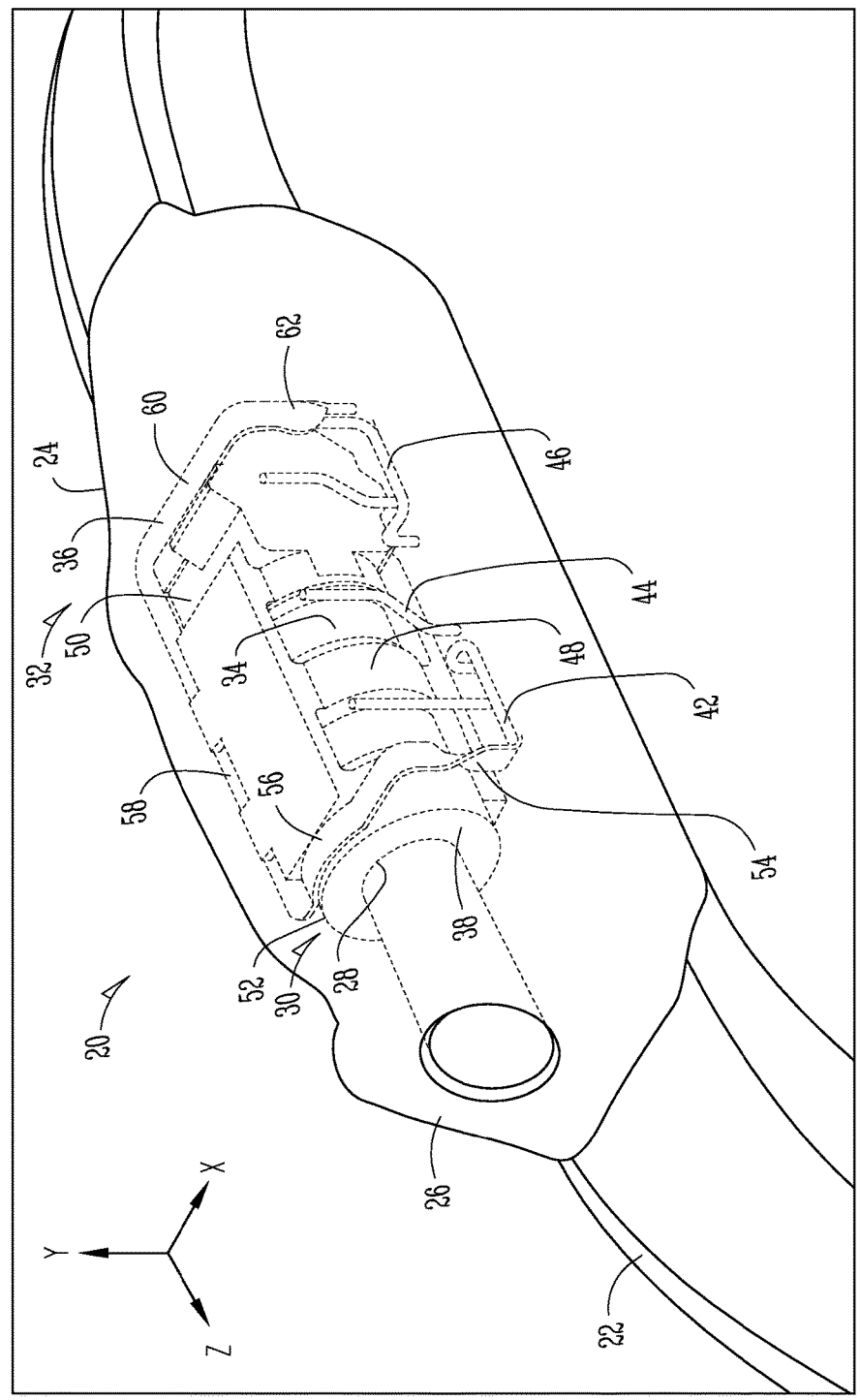
FIG. 4 illustrates a perspective view of an example of a portion of an IMD including a bent loop antenna.

FIG. 4 illustrates an example of a perspective view of a portion of an IMD 20 including a bent loop antenna 36 (hereinafter referred to as "closed loop antenna" and "antenna"). As used herein, a closed loop antenna refers to an antenna where both ends are connected internally to a transceiver creating a constant current loop.

The IMD 20 can include a header 24 including a header core 38, the antenna 36, and a header shell 26. The header core 38 can have a first end 30 and a second end 32 and define a bore 28 to receive a proximal end of a lead. Further, the header core 38 can have a first header surface side 48, a second header surface side 52 opposite the first header surface side 48, and a superior header surface side 50 extending between the first and second header surface sides 48, 52. As shown in FIG. 4, the header core 38 has a shape including substantially flat and curved surfaces. However, it is contemplated that the header core 38 can include any shape such as cylindrical, rectangular, other shapes, and combinations thereof.

The header core 38 can receive connector blocks, for example, connector block 34. The connector blocks can extend partially into the bore 28 such that the connector blocks, when inserted into the header core 38, interface with a lead inserted into the bore 28. The connector blocks can be electrically coupled to the electronic circuitry within the device container 22 via connection wires. For example, the connector block 34 can be electrically coupled to the electronic circuitry via connection wire 44.

Figure 5:
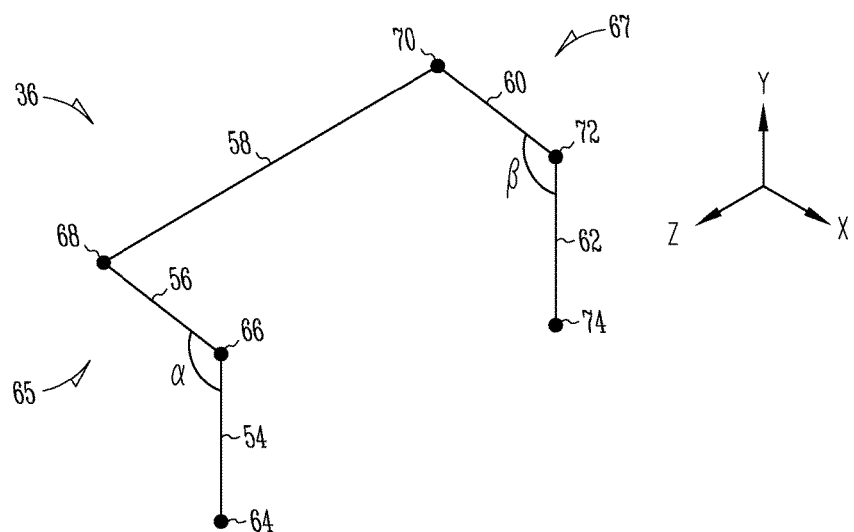
FIG. 5 illustrates an example of a bent loop antenna.

For clarity, FIG. 5 illustrates an example of an antenna 36 individually and is discussed with reference to FIGS. 4 and 5. The antenna 36, as shown in FIGS. 4 and 5, can include a first portion 65 positioned toward the first end 30 of the header core 38 and a second portion 67 positioned toward the second end 32 of the header core 38. The first portion 65 can include a first section 54 extending adjacent to the first header surface side 48 and a second section 56 extending adjacent to the superior header surface side 50. The second portion 67 can include a third section 62 extending adjacent to the first header surface side 48 and a fourth section 60 extending adjacent to the superior header surface side 50. Further, in an example, the antenna 36 can include a third portion 58 connecting the first portion 65 and the second portion 67.

The first section 54 extends from a first connection end 64 to a first transition point 66 and the second section 56 extends from the first transition point to a first intermediate point 68. The third section 62 can extend from a second connection end 74 to a second transition point 72 and the fourth section 60 can extend from the second transition point 72 to a second intermediate point 70. The third portion 58 can extend from the first intermediate point 68 to the second intermediate point 70 to connect the first portion 65 to the second portion 67. The first connection end 64 and the second connection end 74 can be electrically coupled to the electronic module 23 within the device housing 22 via connection wires such as connection wires 42 and 46, respectively.

The first section 54 and the third section 62 are located on a same side of the header core 38, for example, the first header surface side 48. In some examples, the first and third sections 54, 62 can be parallel to each other in a y-z plane. In other examples, the first and third sections 54, 62 can be offset from each other in the y-z plane. For example, the first and third sections 54, 62 can be offset from each other a distance of within a range of about 0.125 inches to about 2 inches. As discussed herein, increasing the area encircled by the antenna 36 can increase radiation characteristics. Therefore, the distance between the first section 54 and the second section 62 can be maximized and determined based on the physical limitations of the header 24. The distance between the first section 54 and the second section 62 can be limited based on the dimensions of the device housing 22, dimensions of the header 25, and the dimensions and design of the header core 38, among others. For example, the header core 38 can include, for example, various connector block openings and can determine where the antenna 36 can be placed in relation to the header core 38. Further, the width, length, and height of the header core 38 and the header shell 26 can determine the maximum space between the first section 54 and the second section 62.

As seen in FIGS. 4 and 5, the antenna 36 can be bent in the y-x plane such that the antenna 36 is disposed in two planes. That is a first portion of the loop formed by the antenna is in a first plane and a second portion of the loop formed by the antenna is in a second plane different from the first. For example, a first portion of the loop can be in the z-y plane, not limited in the x-plane and a second portion of the loop can be in the z-x plane, not limited in the y-plane. In an example, a first portion of the loop such as the first section 54 and the third section 62 can be in the z-y plane, not limited in the x-plane and a second portion of the loop such as the second section 56, the fourth section 60, and the third portion 58 can be in the z-x plane, not limited in the y-plane. Thus, no matter what orientation (or polarization) the signal from the external communicator is received, the closed loop antenna 36 can receive at least some portion of the external signal since the closed loop antenna 36 is positioned in two different planes.

The first portion 65 and the second portion 67 can include a bend where the antenna 36 transitions from the first header surface side 48 to the superior header surface side 50. The angle α formed in the first portion 65 and the angle β formed in the second portion 67, when viewed along the x-y axis, can be within a range of about 45 degrees to about 135 degrees. In some example, angle α and angle β can be the same. In other examples, angle α and angle β can be different from each other. In an example, the transition from the first header surface side 48 to the superior header surface side 50 can include a plurality of bends to transition the antenna 36 from the first header surface side 48 to the superior header surface side 50. Thus, the bend or combination of bends can be within the range of about 45 degrees to about 135 degrees.

In an example, the IMD 20 can include two portions of the antenna 36 positioned along the y-x plane, not being limited in the z-plane. For example, the first portion 65 and the second portion 67 can be positioned in a y-x plane, but can vary within the z-plane. That is, the first connection end 64, the first transition point 66, and the first intermediate point 68 can be in various z-planes. Stated differently, the first connection end 64, the first transition point 66, and the first intermediate point 68 can be positioned at different distances from the first end 30 of the header core 38. Similarly, the second connection end 74, the second transition point 72, and the second intermediate point 70 can be in various z-planes. Stated differently, the second connection end 74, the second transition point 72, and the second intermediate point 70 can be in various z-planes and can be positioned at different distances from the second end 32 of the header core 38.

In an example, the IMD can include only the first section 54 and the third section 62 along the first header surface side 48. That is, the second section 56, the fourth section 60, and the third portion 58 are positioned in a plane different from the first and second sections 54, 62. The third portion 58 can extend between the first portion 65 and the second portion 67. As seen in FIG. 4, the third portion 58 extends along the superior header surface side 50. In an example, the third portion 58 extends along the superior header surface side 50 adjacent to the second header surface side 52 opposite the first header surface side 48. While shown as a straight line, for example, to avoid various protrusions of the header core 38, the third portion 58 can extend back over toward the first header surface side 48.

Figure 6:
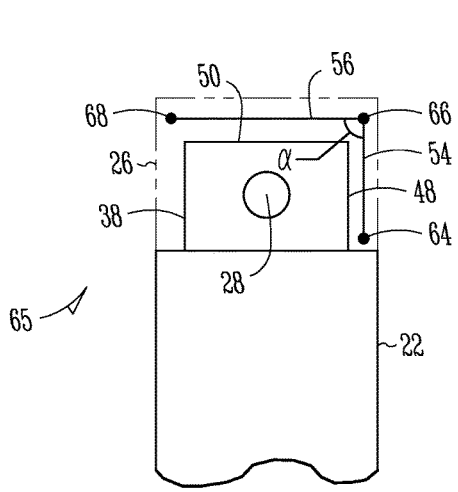
FIG. 6 illustrates a side view from a first end of an example of an IMD including the bent loop antenna.

FIG. 6 illustrates a side view of an example of an IMD including the first portion 65 of the antenna 36. As shown, the antenna 36 is bent in the x-y plane at the first transition point 66. The first section 54 extends adjacent to the first header surface side 48 from the first connection end 64 to first transition point 66. The second section 56 extends adjacent the superior header surface side 50 from the first transition point 66 to the first intermediate point 68. As shown the antenna 36 can bend about the x-y plane having an angle α, as discussed herein. The first transition point 68 can be substantially flush with the second header surface side 52, however, in an example, the first transition point 66 can extend beyond the second header surface side 52 toward an edge of the header shell 28.

Figure 7:
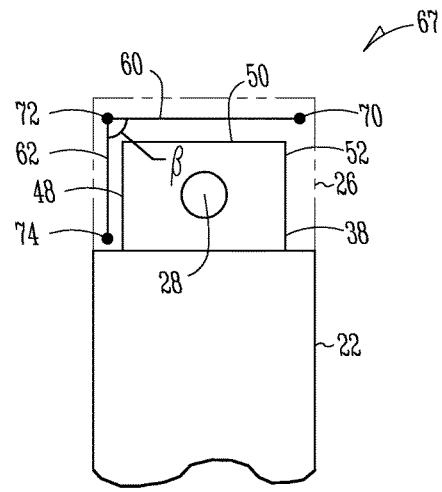
FIG. 7 illustrates a side view from a second end of an example of an IMD including the bent loop antenna.

FIG. 7 illustrates a side view of an example of an IMD including the second portion 67 of the antenna 36. As shown, the antenna 36 is bent in the x-y plane at the second transition point 72. The third section 62 extends adjacent to the first header surface side 48 from the second connection end 74 to second transition point 72. The fourth section 60 extends adjacent the superior header surface side 50 from the second transition point 72 to the second intermediate point 70. As shown the antenna 36 can bend about the x-y plane having an angle β, as discussed herein.

In order to maximize the area enclosed by the antenna 36, the distance, when viewed in the x-y plane, from the first connection end 64 and the first intermediate point 68 (as shown in FIG. 6) and the distance from the second connection end 74 and the second intermediate point 70 (as shown in FIG. 7) should be maximized. Thus, in some examples, the first and second intermediate points 68 and 70 can extend beyond the header core 38. However, the distance from the first and second intermediate points 68 and 70 and the device can 22 can also be maximized. While the examples shown in FIGS. 6 and 7 are shown as having straight lines and forming a 90 degree angle, other configurations are possible as discussed herein with respect to FIGS. 10-18.

Referring to FIG. 5, in an example, the IMD can include can include only the first section 54 and the third section 62 in a y-z plane, not being limited in the x-direction. For example, the first connection end 64 and/or the first transition point 66 can be positioned a distance from the first header surface side 48 that is equal to or different from a distance the second connection end 74 or the second transition point 72 is positioned from the first header surface side 48. In an example, the first and third sections 54, 62 can be mirror images of each other. In other examples, the first and third sections 54, 62 can have different shapes.

In an example, a z-x plane, not limited in the y-direction, can include a portion of an antenna that connects the first and third sections 54, 62. In this example, the z-x plane includes the second section 56, the fourth section 60 and the third portion 58. By having a portion of the antenna in the y-z plane (the first section 54 and the third section 62) and a portion of the antenna in the z-x plane (the second section 56, the fourth section 60 and the third portion 58) the area enclosed by the antenna 36 can be maximized without compromising radiation characteristics.

Figure 8:
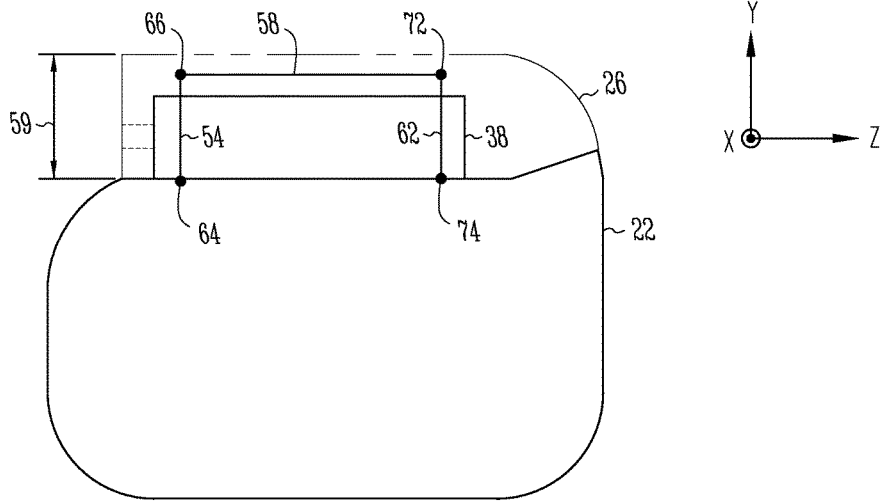
FIG. 8 illustrates a front view of an example of an IMD including the bent loop antenna.

FIG. 8 illustrates a front view of an IMD including the antenna 36. To maximize the area enclosed by the antenna 36, the distance between the first and second transition points 66 and 72 can be maximized. While shown including straight lines, a mixture or straight, curved lines, or stepped lines can be used, as shown in FIGS. 19-27. As discussed herein, IMDs are becoming smaller. In one aspect, the height 59 of the header shell 26 can be reduced thereby making the antenna 36 of the present disclosure even more desirable. For example, the height 59 of the header shell 26 can be within a range of about 0.125 inches to about 2 inches and have an available header shell area of less than 23 cubic inches such as about 20 cubic inches.

Figure 9:
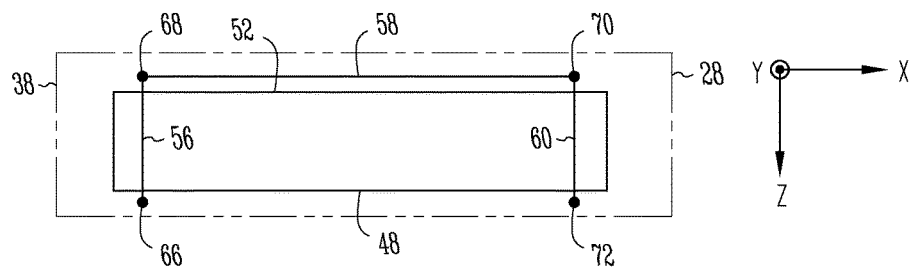
FIG. 9 illustrates a top-down view of an example of a header including the bent loop antenna.

FIG. 9 illustrates a top down view of the IMD 20 including the antenna 36. To maximize the area enclosed by the antenna 36, the distance between the first and second intermediate points 68 and 70 can be maximized. The second section 56, the fourth section 60, and the third portion 58 are in a z-x plane, not limited in the y-plane. That is, either the second section 56, the fourth section 60, the third portion 58, the first or second transition points 66, 72, or the first and second intermediate points 68, 70 can be positioned at different distances from the superior header surface side 50. As shown, the second section 56, the fourth section 60, and the third portion 58 are substantially straight; however, other shapes and configurations can be utilized. For example, the third portion 58 can be curved or bowed along the z-x axis such that the distance between the third portion 58 and the second header surface side 52 varies along the length of the third portion 58. Additionally, the second and fourth sections 56, 60 are shown as being straight; however, they can be curved such that a distance between the second section 56 and a first end 30 of the header core 38 is different from the distance between fourth section 60 and the second end 32 of the header core 38.

Figures 10, 11:
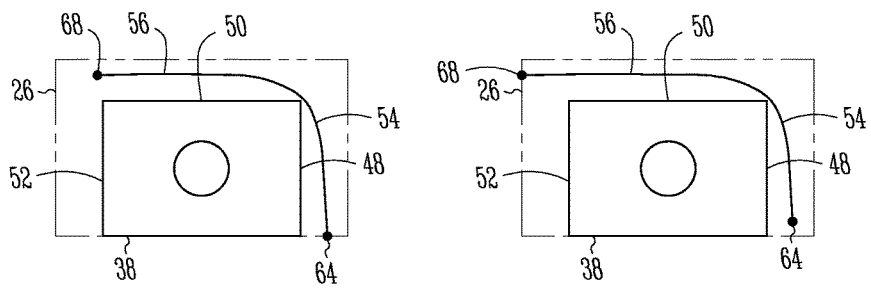
FIG. 10 illustrates a side view of an example of a header including the bent loop antenna.
FIG. 11 illustrates a side view of an example of a header including the bent loop antenna.

FIGS. 10-18 illustrate various examples of the first portion 65 or the second portion 67 viewed from the side including the header core 38 and header shell 26. For simplicity, FIGS. 10-18 are discussed with reference to the first portion 65 including the first section 54 extending from a first connection end 64 to the first transition point 66 and from the first transition point 66 to the first intermediate point 68. As shown in FIGS. 10 and 11, the first portion 65 includes a curved line. In FIG. 10, the first intermediate point 68 can be substantially flush with the second header surface side 52 and in FIG. 11 the first intermediate point 68 can extend beyond the second header surface side 52.

FIG. 12 illustrates an example where the first section 54 includes at least one step. For example, the step can include two sections 69, 71, where section 69 extends substantially parallel to the superior header surface side 50 and the section 71 extends parallel to the first header surface side 48.

In an example, either the first section 54 or the second section 56 can include one or more step. As shown in FIG. 13, the first section 54 and the second section 56 each include a plurality of steps. The first section 54 can include a plurality of steps including sections 51, 53, where the section 51 extends substantially parallel to the first header surface side 48 and the section 53 extends substantially parallel to the superior header surface side 50. The second section 56 includes a plurality of steps including sections 55, 57, where the section 55 extends substantially parallel to the superior header surface side 50 and the section 57 extends substantially parallel to the first header surface side 48.

FIG. 14 illustrates an example where the second section 56 includes an additional portion 50. The portion 50 extends in a direction away from the device 22. FIG. 15 illustrates an example where the second section 56 includes an additional portion 80 that extends toward the device container such that a portion of the first portion 65 is positioned adjacent to the second header surface side 52. Further, in this example, the third portion could be positioned adjacent to the second header surface side 52. In this example, the antenna 36 would be positioned in three different planes. As discussed herein, generally, the distance from the device can 22 and the antenna 36 of the first transition point 68, the third portion 58, and the second transition point 70 can be maximized. While positioning a portion of the antenna 36 along the second header surface side 52 can add additional area encircled by the closed loop antenna 36, the antenna 36 can extend along the second header surface side 52 less than about fifty percent of the second header surface side 52.

Figure 16:
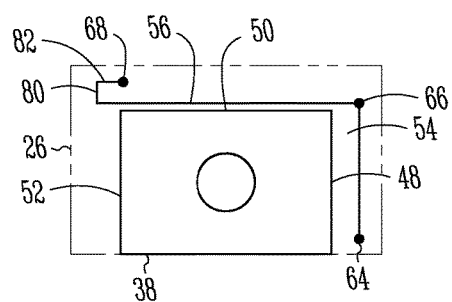
FIG. 16 illustrates a side view of an example of a header including the bent loop antenna.
Figure 17:
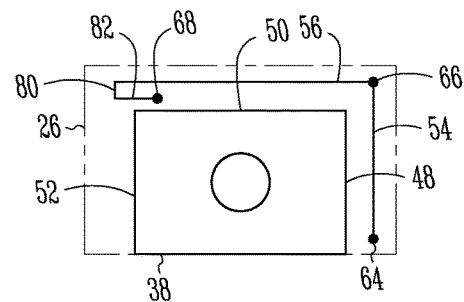
FIG. 17 illustrates a side view of an example of a header including the bent loop antenna.

FIG. 16 illustrates FIG. 14 but with an additional section 82 extending back toward the first header surface side 48. FIG. 17 illustrates FIG. 16 but where the additional section 82 extending back toward the first header surface side 48 is positioned below closer to the superior header surface side 50 as compared to the remaining portion of the second section 56.

Figure 18:
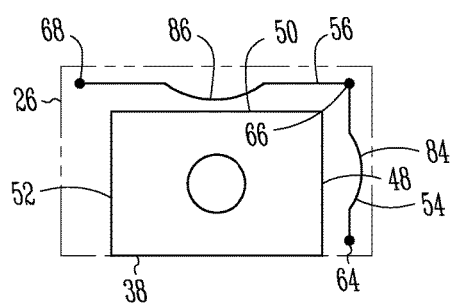
FIG. 18 illustrates a side view of an example of a header including the bent loop antenna.

FIG. 18 illustrates an example including both straight and curved lines. For example, FIG. 18 includes curved line 84 along the first section 54 and curved line 86 along the second section 56. The curved lines 84, 86 can be used to avoid projections or other design features of the header core 38.

FIGS. 19-26 illustrate various examples viewing the IMD from the front including the first section 54, the third section 62, and the third portion 58, as well as the header core 38 and header shell 26. To maximize the area enclosed within the antenna 36, the distance between the transition points 66, 72 can be maximized. FIGS. 19 and 20 illustrate examples, where the first and third sections 54, 62 are curved and the third portion 58 is straight. FIG. 21 illustrates an example, where the first and third sections 54, 62 include an additional step including sections 88 and 90. Sections 88 can extend in a direction substantially parallel the superior header surface side 50 and the sections 90 can extend in a direction substantially perpendicular to the superior header surface side 50. The distance between the first and second connection ends 64, 74 in FIG. 21 can be less than the distance between the first and second connection ends 64, 74 in FIG. 19, for example.

FIGS. 22 and 23 illustrate examples, where the first and third sections 54, 62 include a combination of curved and straight lines. For example, FIGS. 22 and 23 include curved portions 92. In FIG. 22, the curved portions 92 are not mirror images of each other and in FIG. 23, the curved portions 92 are mirror images of each other. In an example, either the first section 54 or the second section 62 can have one or more curved portions 92.

Figure 25:
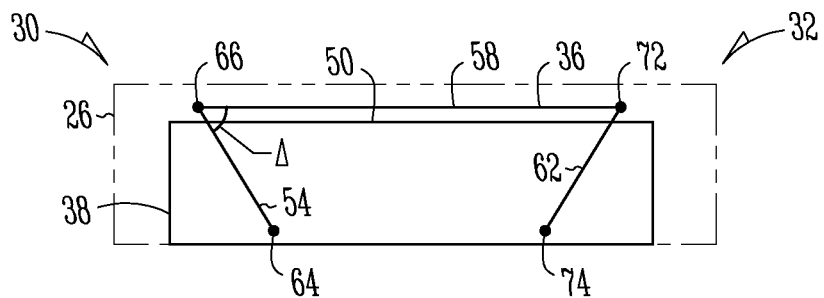
FIG. 25 illustrates a front view of an example of a header including the bent loop antenna.
Figure 26:
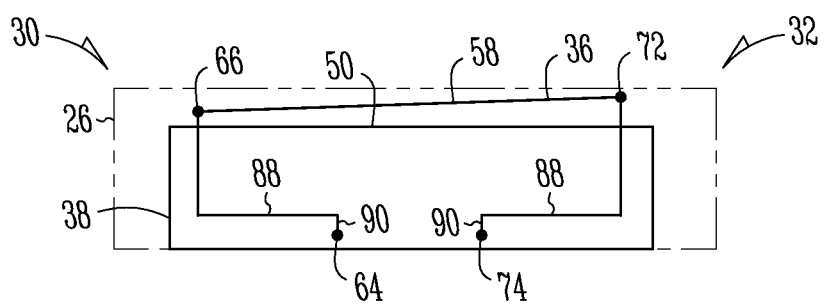
FIG. 26 illustrates a front view of an example of a header including the bent loop antenna.

FIGS. 24 and 25 illustrate examples where the first and third sections 54, 62 are not parallel to each other. In FIG. 24, the first section 54 extends from the first transition point 66 toward the first end 30 of the header core 24 and the third section 62 extends from the second transition point 72 toward the second end 32 of the header core 24. In an example, the first section 54 and the third portion 58 can form angle β. In an example, the angle formed by the third section 62 and the third portion 58 can equal or be different from angle β. FIG. 25 illustrates an example where the first and third sections 54, 62 are not parallel to each other and the first section 54 extends from the first transition point 66 toward the second end 32 of the header core 24 and the third section 72 extends from the second transition point 72 toward the first end 30 of the header core 24. In an example, the first section 54 and the third portion 58 can form angle Δ. In an example, the angle formed by the third section 62 and the third portion 58 can equal or be different from angle Δ. Further, as shown in FIGS. 24 and 25, angle Δ can be less than angle β. FIG. 26 illustrates example 21 except the second transition point 72 is positioned farther away from the superior header surface side 50 than the first transition point 66.

Figure 27:
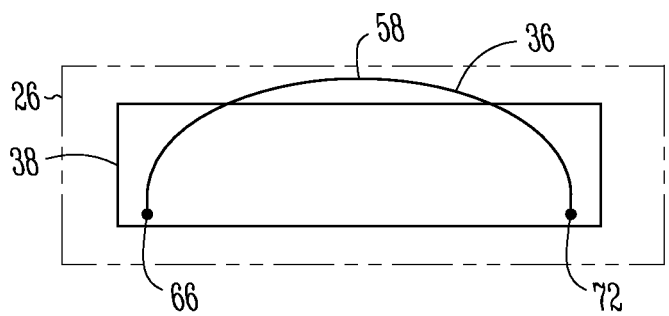
FIG. 27 illustrates a top-down view of an example of a header including the bent loop antenna.
Figure 28:
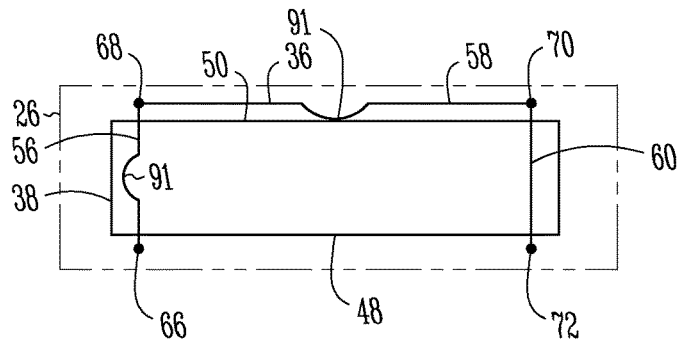
FIG. 28 illustrates a top-down view of an example of a header including the bent loop antenna.
Figure 29:
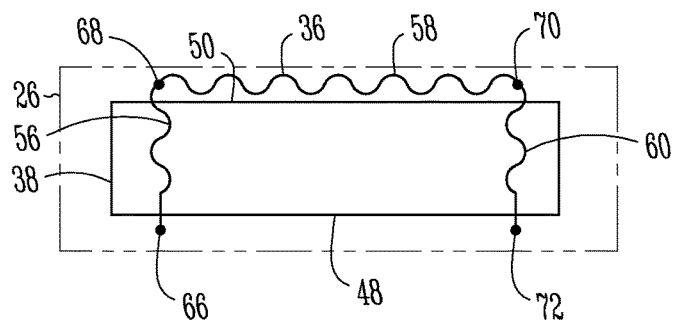
FIG. 29 illustrates a top-down view of an example of a header including the bent loop antenna.
Figure 30:
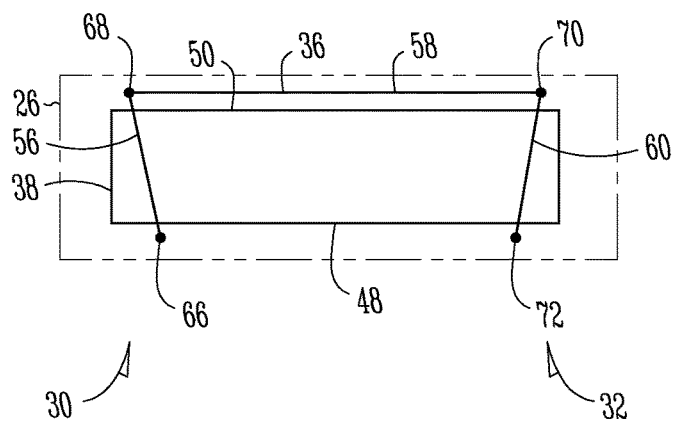
FIG. 30 illustrates a top-down view of an example of a header including the bent loop antenna.

FIGS. 27-30 illustrate various examples of the 1 MB viewed from the top down. In FIG. 27, the antenna doesn't include the second section and the fourth section and the third portion 58 is curved and extends between the first transition point 66 and the second transition point 72 instead of the first and second intermediate points 68 and 70, as shown in FIG. 5. In FIG. 28, second section 56, and the third portion 58 include curved sections 91, while the fourth section 60 is straight. FIG. 29 illustrates an example where the second section 56, the fourth section 60, and the third portion 58 can include a plurality of waves of have a serpentine shape. FIG. 30 illustrates an example where the second section 56 extends from the first intermediate point 68 to the first transition point 66 in a direction toward the second end of the header core 38 and the fourth section 60 extends from the second intermediate point 70 to the second transition point 72 in a direction toward the first end 30 of the header core 38.

While various configurations are possible, the type of configuration used can be based on the type of header core 24 and if any obstructions (e.g., protrusions) are located along any surface of the header.

Figure 31:
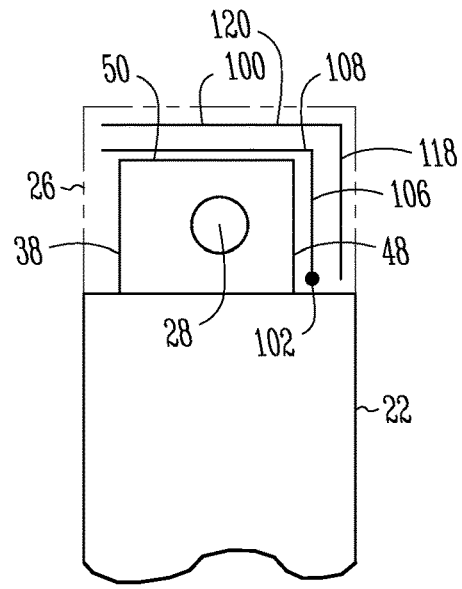
FIG. 31 illustrates a side view of an example of a header including a single antenna including two closed loops.
Figure 32:
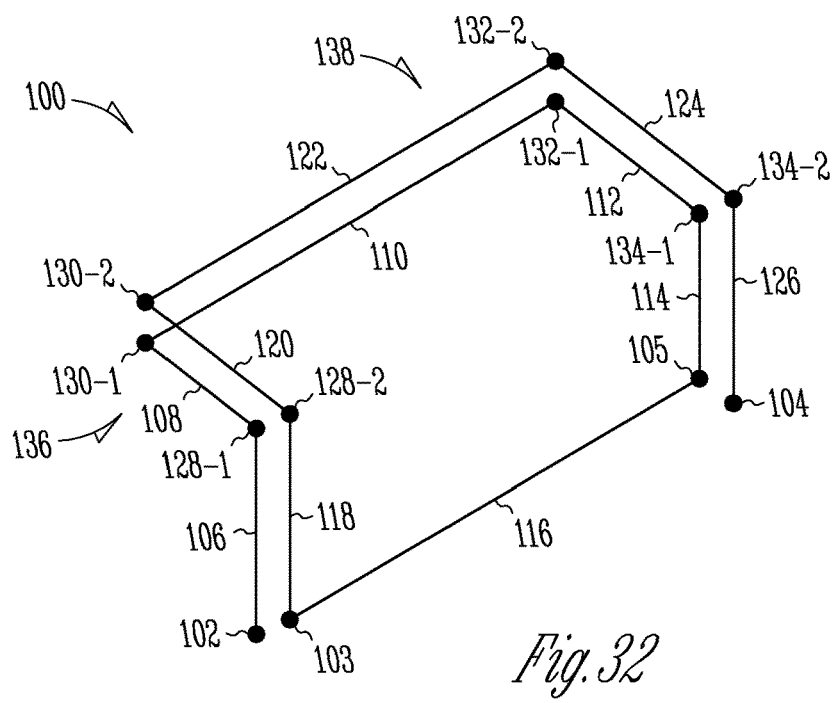
FIG. 32 illustrates a perspective view of an example of a single antenna including to closed loops.

In an example, the header can include more than one antenna or more than one turn of the loop in a single antenna. For example, FIGS. 31 and 32 illustrate an antenna including more than one turn of the loop of a single antenna. FIG. 31 illustrates a portion of an IMD including, the device can 22, the header shell 26, the header core 38, the bore 28 and a single antenna 100 including two loops. As shown in FIGS. 31 and 32, the two loops are formed by a single antenna; however, in other examples, two separate antennas can be stacked together such that the two antennas are parallel to each other. Additionally, while two loops are shown in FIGS. 31 and 32, more than two loops such as three or five loops can be provided.

The antenna 100 as shown in FIGS. 31 and 32 include a first loop portion 136 and a second loop portion 138 formed by a single antenna. The antenna 100 includes a first connection end 102 and a second connection end 104 that can be electrically coupled to circuitry contained within a device container.

The first loop portion 136 can include a first section 106 extending from the first connection end 102 to a first transition point 128-1, a second section 108 extending from the first transition point 128-1 to a first intermediate point 130-1, a third section 110 extending between the first intermediate point 130-1 to the second intermediate point 132-1, a fourth section 112 extending between the second intermediate point 132-1 and the second transition region 134-1, and a fifth section 114 extending between the second transition region 134-1 and a first loop transition point 105. The antenna 100 can include a loop transition section 116 that extends between the first loop transition point 105 and the second loop transition point 103.

The second loop portion 138 of the antenna 100 can start at the second loop transition point 103 and end at the second connection end 104. The second loop portion 138 can include a sixth section 118 extending from the second loop transition point 103 to a third transition point 128-2, a seventh section 120 extending from the third transition point 128-2 to a third intermediate point 130-2, an eighth section 122 extending between the third intermediate point 130-2 to a fourth intermediate point 132-2, a ninth section 124 extending between the fourth intermediate point 132-2 and a fourth transition region 134-2, and a tenth section 126 extending between the fourth transition region 134-2 and the second connection end 104.

In an example, the first loop portion 136 and the second loop portion 138 can have substantially the same shape and be positioned such that the first loop 136 and the second loop 138 are parallel to each other. The first and second loop portions 136, 138 can have any predefined shape as discussed herein.

In an example, the first loop portion 136 can include a first portion including the first section 106 and the second section 108 and the second loop portion 138 can include a first portion including the sixth section 118 and the seventh section 120. In an example, the first portions of the first and second loop portions 136, 138 can be parallel to each other. In an example, the first loop portion 136 can include a second portion including the fourth section 112 and the fifth section 114 and the second loop portion 138 can include a second portion including the ninth section 124 and the tenth section 126. In an example, the second portions of the first and second loop portions 136, 138 can be parallel to each other. Further, the third section 110 of the first loop portion 136 can extend between the first and second portion of the first loop portion 136 and the eighth section 122 of the second loop portion 138 can extend between the first and second portion of the second loop portion 138. In an example, the third section 110 and the eighth section 122 can be parallel to each other.

While shown in FIGS. 31 and 32 as being external to the header core 38, the antenna 100 (or a portion thereof) can be coupled to and/or positioned within a portion of the header core 38. For example, the first loop 136 can be engaged with a slot formed in the header core 36, where the second loop 138 is external to the header core 36.

The present disclosure also provides a method of making an implantable medical device including a bent loop antenna. The method can include providing or obtaining a header core as described herein. For example, the header core can include a first header surface side, a second header surface side, and a superior header surface side extending between the first and second header core sides. The method can include coupling at least one closed loop antenna, as described herein, to the header core, the closed loop antenna disposed in two different planes. The method can include disposing a header shell disposed around the header core, where the header core is a dielectric material.

In an example including two or more antennas, the method can include coupling at least two closed loop antennas to the header core. Further, the method can include obtaining or providing a header core including a slot or engagement tab to couple the two or more antennas to the header core.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable medical device, comprising:
a device container including an electronic module within the device container;
a header core having a first header surface side, a second header surface side, and a superior header surface side extending, along an x-axis, between the first and second header surface sides;
a closed loop antenna, including:
a first loop portion having a predefined shape and being disposed along the first header surface side and the superior header surface side, wherein the first loop portion is bent in an y-x plane such that the first loop portion is disposed in a z-y plane and a z-x plane, the first loop portion including:
a first portion positioned toward a first end of the header core, the first portion including a first section extending adjacent to the first header surface and a second section extending adjacent to the superior header surface;
a second portion positioned toward a second end of the header core, the second portion including a third section extending adjacent to the first header surface and a fourth section extending adjacent to the superior header surface; and a third portion connecting the first portion and the second portion;
a second loop portion having the predefined shape and positioned adjacent to the header core such that the second loop portion is parallel to the first loop portion and disposed along the first header surface side and the superior header surface side, wherein the second loop portion is bent in an y-x plane such that the second loop portion is disposed in a z-y plane and a z-x plane; and
a loop transition section connecting the first loop portion and the second loop portion; and
a header shell disposed around the header core and attached to the device container.

2. The implantable medical device of claim 1, wherein the second loop portion, includes:
a fourth portion positioned toward the first end of the header core, the fourth portion including a fifth section extending adjacent to the first header surface and a sixth section extending adjacent to the superior header surface;
a fifth portion positioned toward the second end of the header core, the fifth portion including a seventh section extending adjacent to the first header surface and an eighth section extending adjacent to the superior header surface; and
a sixth portion connecting the fourth portion and the fifth portion.

3. The implantable medical device of claim 2, wherein the first section includes a first connection end and the seventh section includes a second connection end, the first connection end and the second connection end electrically coupled to the electronic module and are located on a same side of the header core.

4. The implantable medical device of claim 3, wherein the loop transition section extends between the third section of the first loop and the fifth section of the second loop.

5. An implantable medical device, comprising:
a device container including an electronic module within the device container;
a header, the header including:
a header core having a first header surface side, a second header surface side opposite the first header surface side, and a superior header surface side extending between the first and second header surface sides;
a closed loop antenna disposed in two different planes, the closed loop antenna, including:
a first portion positioned toward a first end of the header core, the first portion including a first section extending adjacent to the first header surface side from a first connection end adjacent to the device container, along a y-axis, to a first transition point adjacent the first header surface side and a second section extending adjacent to the superior header surface side from the first transition point, along a x-axis, to a first intermediate point adjacent to the second header surface side;
a second portion positioned toward a second end of the header core, the second portion including a third section extending adjacent to the first header surface side from a second connection end adjacent to the device container, along the y-axis, to a second transition point adjacent to the first header surface side, and a fourth section extending adjacent to the superior header surface side from the second transition point, along the x-axis, to a second intermediate point adjacent to the second header surface; and
a third portion connecting the first portion and the second portion and extending from the first intermediate point, along a z-axis, to the second intermediate point,
wherein, when viewed along a x-y plane, the first portion and the second portion include a bend transitioning the antenna from the first header surface side to the superior header surface side at the first and second transition points; and
a header shell disposed around the header core and attached to the device container.

6. The implantable medical device of claim 5, wherein the first connection end and the second connection end are electrically coupled to the electronic module.

7. The implantable medical device of claim 5, wherein, when viewed along a z-x plane, the antenna includes two bends at the first intermediate point and the second intermediate point.

8. The implantable medical device of claim 7, wherein an angle of the bend at the first and second transition points, when viewed along the x-y plane, is within a range of about 45 degrees to about 135 degrees.

9. The implantable medical device of claim 5, wherein the first section and the third section are in a z-y plane, not limited along the x-axis, and the second section, the fourth section, and the third portion are in a z-x plane, not limited in along the y-axis.

10. The implantable medical device of claim 5, wherein the first header surface side includes only the first section and the third section of the antenna.

11. The implantable medical device of claim 5, wherein the header shell is formed of a dielectric material.

12. A method of making an implantable medical device including a bent loop antenna, comprising:
providing or obtaining a header core having a first header surface side, a second header surface side, and a superior header surface side extending between the first and second header core sides;
coupling at least one closed loop antenna to the header core, the closed loop antenna disposed in two different planes and including:
a first portion positioned toward a first end of the header core, the first portion including a first section extending adjacent to the first header surface side from a first connection end adjacent to the device container, along a y-axis; to a first transition point adjacent the first header surface side and a second section extending adjacent to the superior header surface side from the first transition point, along a x-axis, to a first intermediate point adjacent to the second header surface side;
a second portion positioned toward a second end of the header core, the second portion including a third section extending adjacent to the first header surface side from a second connection end adjacent to the device container, along the y-axis, to a second transition point adjacent to the first header surface side; and a fourth section extending adjacent to the superior header surface side from the second transition point, along the x-axis, to a second intermediate point adjacent to the second header surface; and
a third portion connecting the first portion and the second portion and extending from the first intermediate point, along a z-axis, to the second intermediate point, and disposing a header shell disposed around the header core.

13. The method of claim 12, wherein the at least one closed loop antenna is a first closed loop antenna, the method includes:
   coupling a second closed loop antenna to the header core.

14. The method of claim 13, wherein the first closed loop antenna and the second closed loop antenna have a same predefined shape and are coupled to the header core such that the first closed loop antenna is parallel to the second closed loop antenna.

* * * * *